United States Patent [19]

Haindl

[11] Patent Number: 4,981,475
[45] Date of Patent: Jan. 1, 1991

[54] DEVICE FOR FASTENING A CATHETER

[75] Inventor: Hans-Guenter Haindl, Melsungen, Fed. Rep. of Germany

[73] Assignee: B. Braun Melsungen AG, Melsungen, Fed. Rep. of Germany

[21] Appl. No.: 313,707

[22] Filed: Feb. 22, 1989

[30] Foreign Application Priority Data

Mar. 2, 1988 [DE] Fed. Rep. of Germany ... 8802756[U]

[51] Int. Cl.⁵ .............................................. A61M 5/32
[52] U.S. Cl. ............................. 604/174; 128/DIG. 26
[58] Field of Search ............................... 128/DIG. 26; 604/174–180

[56] References Cited

U.S. PATENT DOCUMENTS

| | | | |
|---|---|---|---|
| 2,727,512 | 12/1955 | Muller | 128/DIG. 26 |
| 2,882,898 | 4/1959 | Holmes | 604/174 |
| 3,568,679 | 3/1971 | Reif | 128/DIG. 26 |
| 3,722,508 | 3/1973 | Roberts | 128/DIG. 26 |
| 3,834,380 | 9/1974 | Boyd | 128/DIG. 26 |
| 4,209,015 | 6/1980 | Wicks | 604/174 |
| 4,435,174 | 3/1984 | Redmond et al. | 128/DIG. 26 |
| 4,632,670 | 12/1986 | Mueller, Jr. | 128/DIG. 26 |
| 4,645,492 | 2/1987 | Weeks | 128/DIG. 26 |
| 4,645,495 | 2/1987 | Vaillancourt | 604/180 |
| 4,683,895 | 8/1987 | Pohndorf | 604/174 |

FOREIGN PATENT DOCUMENTS

| | | |
|---|---|---|
| 7801811 | 7/1978 | Fed. Rep. of Germany . |
| 8204827 | 7/1982 | Fed. Rep. of Germany . |
| 3643985 | 12/1987 | Fed. Rep. of Germany . |

Primary Examiner—Stephen C. Pellegrino
Assistant Examiner—Ralph Lewis
Attorney, Agent, or Firm—Spensley Horn Jubas & Lubitz

[57] ABSTRACT

In a device for fastening a transcutaneous or implanted catheter, a plate of bendable material is provided with a soft flexible, button-shaped plate body that is defined by two lateral faces without projections. The plate body is provided with a clamping groove, open at both ends and axially slotted, for accommodating a catheter. The plate body is provided with a locking device for the axial slot, which consists of a leaf spring being embedded and fixed in the plate body on the closed side of the clamping groove which it bridges. Such a device reliably fixes transcutaneous or implanted catheters of any kind in a manner well tolerated by the body.

11 Claims, 2 Drawing Sheets

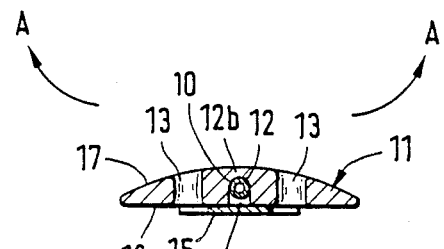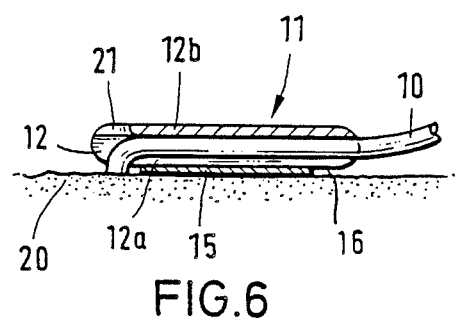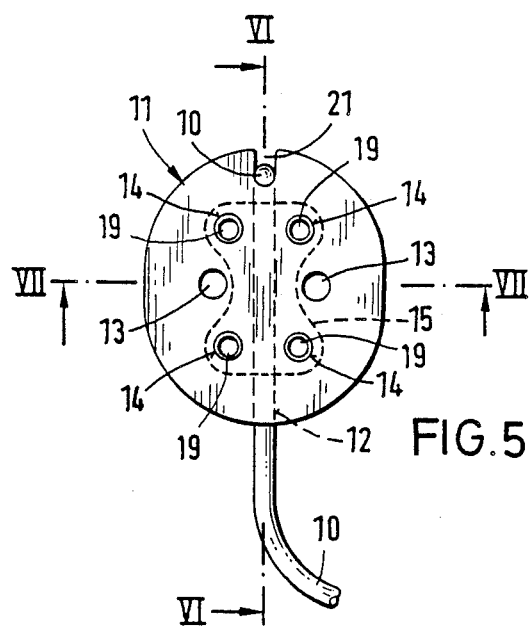

DEVICE FOR FASTENING A CATHETER

BACKGROUND OF THE INVENTION

1. Field of the Invention

The invention relates to a device for fastening a transcutaneous or an implanted catheter, consisting of a plate of bendable material provided with an axially slotted clamping groove, open at both ends, for the catheter.

2. Description of Related Art

A secure fixing of a catheter, be it a peridural catheter or a vascular catheter, should be made as close as possible to the point of puncturing. Implanted catheters, as well, should be fixed at certain points to avoid dislocations.

Fixing devices developed for this purpose can be roughly divided into adhesive devices and clamping devices. Adhesive devices use adhesive foils that fasten the portion of the catheter issuing from the point of puncturing directly on the skin or, in a sandwich-like arrangement, fix that catheter portion between them by adhesion (German Laid Open No. 36 43 985). However, such adhesive devices do not work, e.g., with peridural catheters. This is partly due to the fact that these adhesives do not stick well on common catheter materials (like polyamide). This is also due to the fact that strong adhesive agents cannot be used in the area of the wound. With implanted catheters, adhesives cannot be used at all.

A known clamping device comprises a clip having two perforated clamping plates with clamp elements for fixing the catheter. The perforations allow the clip to be sewn on the skin (German Utility Model No. 82 04 827). Both clamping plates are made of rigid plastic material, so that the clip is rigid and hard. For this reason it cannot be used as an implant. Neither can it be used in the region of the back of a patient, since a patient can not lie on the rigid clips. The stiffness of the clip reduces its fixability to polyurethane catheters (the surface of which, due to their material, has a certain stickiness). Polyamide catheters, e.g., peridural catheters, are not reliably fixed in the rigid clip, due to their lack of surface stickiness.

Further, the clamping device of the above-mentioned type is known (German Utility Model No. 78 01 811). In this case, loop-like bending provides a strip-shaped, thin plate with several parallel clamping grooves having diameters smaller than the outer diameter of the catheter to be fixed, in order to achieve a clamping effect. The axial slot of each clamping groove runs in the flat bottom face of the plate. Bending the plate widens the axial slot of each clamping groove in order to lay in catheter portions. In the straight state, the plate, with its flat lateral surface facing the skin, is fastened to the surface of the skin with adhesive plasters. This known fixing device cannot be used as an implant, not only because of the problematic adhesive fixing, but also because of the thinness of the plate which requires a supporting surface for its flat lateral surface, so that it is not bent such that the clamping grooves are widened, thus losing their clamping effect on the catheter.

It is an object of the present invention to improve the fixing device according to German Utility Model No. 78 01 811 such that it fixes transcutaneous and implanted catheters of any kind in a reliable manner, well tolerated by the body.

SUMMARY OF THE INVENTION

In accordance with the present invention, this and other objectives are achieved by providing the plate with a soft, flexible, button-shaped body defined by two lateral faces without projections, in which plate body the clamping groove is recessed.

In the center of the soft, flexible, button-shaped plate body, preferably made of polyurethane, the clamping groove extends from one end to the other. The height of the clamping groove corresponds to the thickness of the plate body, with the exception of a base ridge at its closed base. The outer surface of the base ridge of the clamping groove lies flush in one of the lateral faces of the plate body, which is preferably convex. The axial slot opening of the clamping groove is flush with the other lateral face of the plate body, which can be substantially flat.

Bending the plate body widens the clamping device, so that the catheter can be laid in. On the elastic springback of the soft plate body, the lateral flanks of the clamping groove resiliently press the catheter slightly, thus keeping it connected with the plate body.

The soft flexibility of the button-shaped plate body is the primary reason why it is also suitable as a fastening member for catheters without an adhesive surface (which, like peridural catheters, are made of polyamide). Since it has no projections on either side and due to its softness, the button-shaped plate body can be applied in the region of a patient's back, without hindering the patient's resting. Since, given a sufficient thickness of the plate body and of the base ridge of the clamping groove, the inherent resilience of the soft flexible material suffices for the hold of the clamping groove, the fastening device can be successfully used for implanted catheters as well. In such case, the fixing can be achieved by sewing. The plate body may be sewed to the surface of the skin or fastened by an adhesive device.

To facilitate the sewing-on of the plate body to the skin or in tissue, the plate body has both longitudinal sides of the clamping groove provided with through going holes. The holes also serve to strengthen and maintain the clamping pressure of the clamping groove by allowing the application of two filament ligatures through pairs of holes such that the ligatures bridge the clamping groove.

Expediently, the plate body is enlarged in the central portion including the clamping groove. It may also be provided that the lateral face directed away from the axial slot of the clamping groove is convex transverse to the longitudinal axis of the clamping groove. In this manner, one arrives at an augmented clamping ability of the plate body in the area of the clamping groove. The outer edges of the plate body, parallel to the clamping groove, are flattened, which is advantageous for the fastening of the plate body on the skin.

Preferably, the cross section of the clamping groove is substantially circular. Alternatively, it may also be almost U-shaped. In the first case, the axial slot of the clamping device is provided between two lips that may be in mutual contact. In the second case, the axial slot is more open. Preferably, both embodiments have at least one end of the clamping groove provided with at least one passage for a bent catheter, transverse to the thickness of the plate body. The passage may be a hole or a slot open towards the end of the plate. These passages allow the catheter fixed in the clamping groove to be lead out of the plate body at a right angle; i.e., perpendicular to the plane of the plate body. If necessary, the plate body can thus be fixed to the skin or in the underlying tissue directly over the point of entry of the catheter. The support at the bending point protects the catheter from kinking.

If holding the clamping device together with ligature is not desired, a locking device according to the invention may be used for the axial slot of the clamping groove. The locking device may consist of a tie with projections that bridges the axial slot of the clamping groove, the projections being snapped into some of the holes of the plate body. The tie may be provided as a plastic bridge with four projections that snap and fit into four holes of the plate body. A metal clamp, shaped accordingly, may be used as well.

A preferred alternative embodiment of the locking device uses a leaf spring that is embedded and fixed in the plate body on the closed side of the clamping groove which it bridges. Such a locking device is particularly advantageous, since it requires no handling by a user. It is permanently integrated in the plate body and supports the resilience of the polyurethane material of the plate body for holding together the clamping groove with a catheter laid in. The leaf spring may be provided as an arched symmetric metal lamella, having both lateral legs provided with holes that coincide with passages in the plate body or into which polyurethane material penetrates, thereby achieving an improved anchoring of the leaf spring in the plate body. However, the leaf spring must not cover the holes in the plate body that allow the sewing of the plate body in tissue or on the skin. For this reason, either its shape and/or its dimensions should be selected accordingly, or the holes in the leaf spring should coincide with the passages in the plate body.

BRIEF DESCRIPTION OF THE DRAWINGS

A detailed description of various embodiments of the invention will be made with reference to the accompanying drawings, wherein like numerals designate corresponding parts in the several figures.

FIGS. 5, 6 and 7 show views of a further embodiment of the plate body with locking device, corresponding to FIGS. 1 and 3.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

Figure 1:
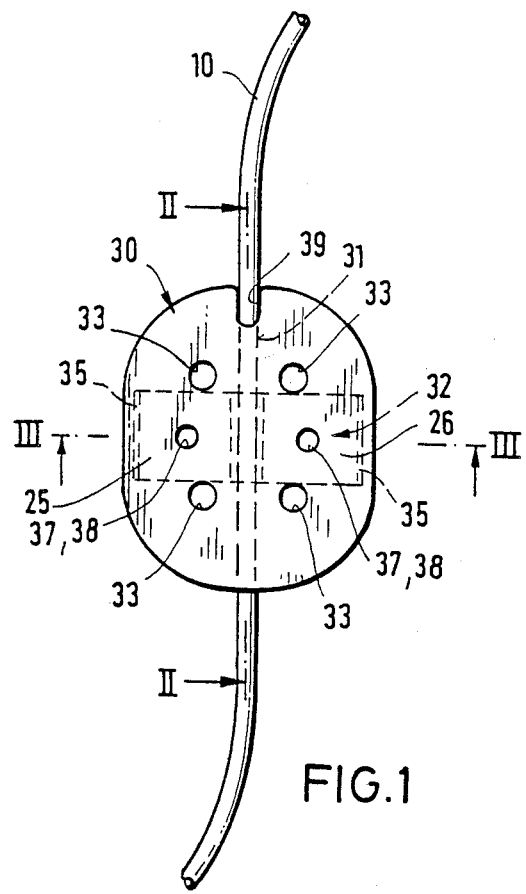
FIG. 1 shows a top view of an embodiment of the fastening device with a laid-in catheter.
Figure 4:
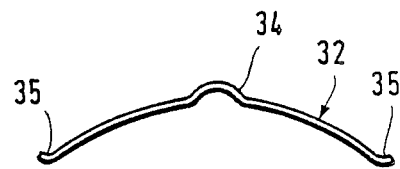
FIG. 4 shows a schematic lateral view of the basic shape of an embodiment of the leaf spring before extrusion-coating.

As illustrated in FIG. 1, an embodiment of the device for fastening a transcutaneous or an implanted catheter 10 (which may be a peridural polyamide catheter that is not easily attachable by adhesion) substantially comprises a soft, flexible button-shaped plate body 30, preferably of polyurethane, which is traversed from one end to the other by a straight clamping groove 31 with an axial slot 31a. In top view, the plate body 30 is substantially rectangular in shape with round corners. On both sides of the clamping groove 31 the plate body 30 is provided with mutually opposite pairs of throughgoing holes 33. The holes 33 allow a fixing of the plate body 30 on the skin or in tissue by ligature.

The plate body 30 has a slight concave curve on the lateral face 36 that is provided with the axial slot 31a of the clamping groove 31. The cross section of the opposite lateral face 29 containing the flush base ridge 31b of the clamping groove 31 has a slight convex curve. The respective curved portions extend from one end of the clamping groove 31 to the other. The plate body 30 flattens towards its two longitudinal edges that extend generally parallel to the clamping groove 31.

In the embodiment shown in FIGS. 1 to 4, the clamping groove 31 has a circular cross section and it extends from one end of the plate body 30 to the other end with a constant diameter. The axial slot 31a is defined by two lips 28 that almost meet. In the illustrated embodiment, the two lips 28 lie flush in the lower lateral face 36 of the plate body 30. In order to open the plate body 30 for insertion of a catheter 10 into the clamping groove 31, the plate body is bent in the direction of the two arrows A (FIG. 3) and the catheter 10 is laterally pressed into the clamping groove 31. The diameter of the clamping groove 31 is dimensioned such that it is slightly less than that of the catheter 10 to be fixed. Slight pressure is applied to the catheter 10 by the plate body 30 when the latter resiliently returns to its initial position. This pressure keeps the catheter 10 in connection with the plate body 30.

Figure 3:
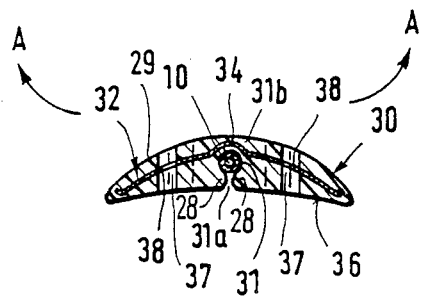
FIG. 3 shows a cross section of an embodiment of the plate body according to FIG. 1 along the line III—III.

A locking device in form of a metal leaf spring 32 is embedded by extrusion-coating in the plate body 30 of soft flexible plastic material to thereby increase the clamping effect of the clamping groove on a laid-in catheter 10. The metal leaf spring 32 is provided as a curved lamella that is shorter than the plate body 30 and extends in the central part of the plate body 30 transverse to the clamping groove 31. The central bulging portion 34 of the leaf spring 32 extends transversely through the base ridge 31b of the plate body 30. As shown in FIGS. 1 and 3, the two ends 35 of the legs 25 and 26 of the leaf spring 32 are embedded in the lip-like flattened lateral edge portions of the plate body 30. Preferably, the two ends 35 are slightly curved against the bend of the leaf spring 32, so that they do not cause any projections on the flat lower surface 36 of the plate body 30 and the resilient effect of the leaf spring 32 is supported. Both legs 25 and 26 of the leaf spring 32 are provided with a hole 38, respectively, that coincides with corresponding passages 37 (cf. FIGS. 1 and 3) in the plate body 30. The holes 38 may be used—holes 33—to sew the plate body 30 on the skin or in tissue. If necessary, the holes 38 may be used to improve the anchoring of the leaf spring 32 in the plate body 30 by taking up stoppers of polyurethane material during the extrusion-coating of the leaf spring.

Figure 2:
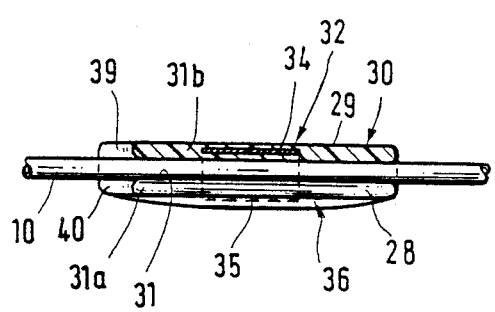
FIG. 2 shows a longitudinal section of an embodiment of the plate body along the line II—II of FIG. 1.

In order to avoid kinking when connecting the catheter 10 issuing from the skin or from tissue to the plate body 30 in a right-angled bend (as suggested in the embodiment of FIGS. 5-7), the plate body 30 is provided at the end of the clamping groove 31 with a passage 39 in the base ridge 31b of the clamping groove 31. In the embodiment illustrated, the passage 39 is provided as a slot open towards the end of the plate body 30. A second, almost congruent passage 40 at the same end of the clamping groove 31 is provided as a recess in the lips 28 (FIG. 2). In order to protect the catheter 10, the passages 39 and 40 are rounded at the side facing the clamping groove 31. The passages 39 and 40 open towards both lateral faces 29 and 36 of the plate body 30. This allows a bending of the catheter 10 that is independent of the position of the plate body 30 relative to the surface it is fastened on, i.e., the plate body 30—different from the arrangement illustrated—may also be attached such that the axial slot 31a of the clamping groove 31 points upward, whereas the base ridge 31b points downward.

In the embodiment illustrated in FIGS. 5, 6 and 7, a plate body 11 is also made of soft flexible plastic material, preferably polyurethane. In top view, the plate body 11 is almost oval. In the direction of its longer axis, the plate body 11 is provided with a straight clamping groove 12 having an axial slot 12a. The axial slot 12a is provided in a flat lateral face 16 (the lower face in FIG. 7). The opposite lateral face 17 of the plate body 11 extends transverse to the clamping groove 12 and is curved convexly, so that the two longitudinal edges of the plate body 11 that are parallel to the clamping groove 12 have a higher flexibility and softness, due to a lesser thickness of material. The plate body 11 is provided with mutually opposite pairs of throughgoing holes 13 and 14 on both sides of the clamping groove 12. The holes 13 allow the fastening of the plate body 11 on the skin or in tissue. The two pairs of holes 14, separated by the pair of holes 13, serve the application of two filament ligatures for transversely holding together the U-shaped clamping groove 12 with a laid-in catheter 10.

Alternatively or additionally, a plastic tie 15 may be provided on the lateral face 16 to bridge the clamping groove 12. The tie 15 may be of hyperbolic shape in order not to cover the two holes 13 of the plate body 11 (FIG. 5). The tie 15 is a flat plate with four projections 19 on one side, which may be snapped into the holes 14 of the plate body 11 like snap fasteners or which may be in tight fitting engagement with the holes 14. An additional hold for the catheter 10 laid into the clamping groove 12 is provided by the sticky surface of the polyurethane material of the plate body 11, since the walls of the U-shaped clamping groove 12 elastically press against the catheter 10 which is slightly bigger in dimension than the diameter of the clamping groove. In order to insert the catheter 10 into the clamping groove 12 prior to the application of the tie 15, the plate body 11 is bent around the base ridge 12b of the clamping groove 12 in the direction of the two arrows A (FIG. 7), so that the clamping groove 12 is widened. The proper elasticity of the material of the plate body 11 effects the reset of the plate body into the initial position in which the clamping effect of the clamping groove 12 is achieved and in which the tie 15 may be applied.

The plate body 11 may be fastened to the skin 20 as illustrated in FIG. 6 or in the turned position. When the plate body is fastened in the turned position, a passage 21, in the form of an open recessed slot in the base ridge 12b at one end of the clamping groove 12, serves as a protection against kinking of the catheter 10. A certain slight clamping effect exists between the bent catheter 10 and the passage 21. In order to protect the catheter 10, the passage 21 is rounded at the side facing the clamping groove 12.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A device for fastening a catheter, comprising:
   a plate body of soft, flexible material defining a clamping groove fully recessed in the plate body having an axial slot and two open ends and being configured to receive a catheter,
   a first lateral face and a second lateral face, the first lateral face and the second lateral face defining a distance therebetween, the first lateral face being spaced relatively closer to the axial slot than the second lateral face,
   the second lateral face being curved convexly and defining two longitudinal sides extending generally parallel to the clamping groove, the distance between the first lateral face and the second lateral face generally diminishing with increasing distance from the clamping groove.

2. A device according to claim 1, wherein the plate body further defines at least one hole on each side of the clamping groove.

3. A device according to claim 1, wherein the plate body further defines a relatively enlarged section in the region adjacent the clamping groove.

4. A device according to claim 1, wherein the clamping groove has a substantially circular cross section and wherein the plate body further defines a bent catheter passage adjacent one end of the clamping groove and extending transversely to the plate body thickness, whereby a catheter fixed in the clamping groove may exit the plate body at a right angle to the plate body.

5. A device according to claim 1, wherein the clamping groove has a substantially U-shaped cross section and wherein the plate body further defines a bent catheter passage adjacent one end of the clamping groove and extending transversely to the plate body thickness, whereby a catheter fixed in the clamping groove may exit the plate body at a right angle to the plate body.

6. A device according to claim 1, further comprising locking means for locking the axial slot of the clamping groove.

7. A device according to claim 6, wherein the plate body further defines at least one hole on each side of the clamping groove and wherein the locking means comprises a tie configured to bridge the axial slot of the clamping groove and having projections configured to be received by the at least one hole on each side of the clamping groove.

8. A device according to claim 1 wherein the plate body is made of polyurethane.

9. A device for fastening a catheter, comprising:
   a plate body of soft, flexible material defining two smooth, lateral faces and further defining a clamping groove fully recessed in the plate body having an axial slot and two open ends and being configured to received a catheter, and
   locking means for locking the axial slot of the clamping groove, wherein the locking means comprises a leaf spring embedded in the plate body and bridging the clamping groove.

10. A device according to claim 9, wherein the plate body further defines at least one passage on each side of the clamping groove and wherein the leaf spring comprises a curved, symmetric metal lamella having two legs provided with holes that coincide with the at least one passage on each side of the clamping groove.

11. A device according to claim 10, wherein the legs of the leaf spring each end in a bow curved in a direction opposite to the curve of the leaf spring.

* * * * *